United States Patent [19]

Fish

[11] Patent Number: 6,155,974
[45] Date of Patent: Dec. 5, 2000

[54] WIRELESS MULTIPLEXED BRAIN WAVE MONITORING SYSTEM AND METHOD

[75] Inventor: Charles Michael Fish, Teaneck, N.J.

[73] Assignees: Sony Corporation, Tokyo, Japan; Sony Electronics, Inc., Park Ridge, N.J.

[21] Appl. No.: 08/904,589

[22] Filed: Aug. 1, 1997

[51] Int. Cl.⁷ .................................. A61B 5/00; A61B 5/04
[52] U.S. Cl. ........................ 600/300; 600/544; 128/903
[58] Field of Search ..................... 128/903, 904; 600/383, 544, 300, 301, 545

[56] References Cited

U.S. PATENT DOCUMENTS

| | | | |
|---|---|---|---|
| 4,173,971 | 11/1979 | Karz | 128/904 |
| 4,799,062 | 1/1989 | Sanderford, Jr. et al. | 342/450 |
| 5,273,037 | 12/1993 | Itil et al. | 600/383 |
| 5,291,888 | 3/1994 | Tucker | 128/644 |
| 5,357,957 | 10/1994 | Itil et al. | 600/383 |
| 5,441,047 | 8/1995 | David et al. | 128/670 |
| 5,513,130 | 4/1996 | Redmond | 600/544 |
| 5,540,235 | 7/1996 | Wilson | 600/545 |
| 5,552,791 | 9/1996 | Metal | 342/174 |
| 5,564,433 | 10/1996 | Thornton | 600/544 |
| 5,730,146 | 3/1998 | Itil et al. | 600/545 |
| 5,759,044 | 6/1998 | Redmond | 600/544 |
| 5,771,001 | 6/1998 | Cobb | 340/573 |
| 5,862,803 | 1/1999 | Besson et al. | 600/545 |

*Primary Examiner*—Cary O'Connor
*Assistant Examiner*—Michael Aszorino
*Attorney, Agent, or Firm*—Ronald P. Kananen; Rader, Fishman & Grauer

[57] ABSTRACT

A novel method and apparatus of monitoring brain wave activity in a patient allows the patient to be mobile during the monitoring. A size adjustable skull cap is fitted to the patient. In the skull cap a plurality of sensors monitor the patient's brain waves and transmit the data with a polydirectional antenna over a wireless connection to a supporting system. The supporting system processes, correlates and allows a physician to review, edit and annotate the data obtained from monitoring the patient.

32 Claims, 6 Drawing Sheets

WIRELESS MULTIPLEXED BRAIN WAVE MONITORING SYSTEM AND METHOD

FIELD OF THE INVENTION

The present invention involves the field of monitoring brain wave activity. More particularly, the present invention relates to a wireless method and system of monitoring brain wave activity in a patient.

BACKGROUND OF THE INVENTION

In a variety of diagnostic situations, a physician may need to monitor the brain wave activity of a patient in order to determine the proper course of treatment. Conventional brain wave monitoring systems, known as electroencephalographs, create electroencephalograms ("EEGs"). EEGs are graphs of the fluctuating brain wave activity of the patient being monitored. Electroencephalographs create EEGs by receiving electric signals from a series of electrodes glued to the scalp of the patient at a variety of points about the patient's scalp.

These electrodes are typically wired to a processing device and provide an electric signal which is influenced by the electric signals of the brain. The signals from the electrodes can be used by the processing device to create an EEG. EEG's may be displayed on a screen or printed on a roll of paper. The physician can then review the EEG for evidence of abnormal brain activity in the patient. Existing EEGs are also sometimes supplemented by footage of the patient filmed with a video camera and recorded with video tape recorder (VTR) on a conventional tape medium. However, the footage and the EEG must be temporally coordinated before being reviewed by a physician, and the review process can still be troublesome and very time-consuming.

Conventional electroencephalographs also suffer from a number of additional drawbacks. For example, the process of gluing electrodes to the scalp of a patient prior to monitoring is a messy and labor-intensive process that must be carried out by a trained professional. Moreover, standard adhesives and solvents used for this purpose may produce toxic fumes and therefore the gluing cannot occur in many areas of a hospital. Alternatively, electrodes are sometimes inserted below the scalp, an invasive process which is better avoided if possible.

Additionally, if the physician is looking for a brain wave anomaly that occurs irregularly or infrequently, the patient may need to be monitored for a lengthy period of time. This becomes difficult for the patient who must remain largely immobile while wired to the processing device of the electroencephalograph.

Accordingly, there is a need for an improved apparatus and method for monitoring brain wave activity that can overcome these and other problems inherent in the prior art.

SUMMARY OF THE INVENTION

It is an object of the present invention to meet the above-described needs and others. It is an object of the present invention to provide a wireless brain wave monitoring apparatus and method.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve the stated and other objects of the present invention, as embodied and described below, the invention may encompass a system for monitoring brain waves including: a plurality of sensors for generating signals based on brain waves; a wireless link for transmitting the signals to a processor; and a processor for receiving the transmitted signals and for processing the signals. The plurality of sensors may be disposed in a piece of headgear, i.e., skull cap or a helmet. The headgear may include a polydirectional antenna for establishing the wireless link. The headgear is preferably made adjustable to a range of sizes.

The headgear may further include a multiplexer for multiplexing the signals prior to transmission, and an encoder for encoding the signals prior to transmission. The circuitry on the headgear may include a test port through which test signals may be input to test or initialize the operation of the circuitry.

The system of the present invention may also include a video camera for providing video and audio feed of a patient whose brain waves are being monitored. In addition to the camera, the system may have a plurality of receivers for receiving the transmitted signals; a processing circuit for receiving the video and audio feed; a mixer for mixing the signals and the feed; and a synchronizing circuit which controls the mixer, causing the mixer to temporally correlate the signals and the feed. The processing circuit may also generate a camera control signal to control the operation of the video camera.

The processor of the system may also include a non-volatile data storage unit for storing a correlated signal output by the mixer. A signal compressor may be used for compressing the correlated signal prior to storage in the non-volatile data storage unit. A computer may be included for editing, annotating or analyzing the correlated signal stored in the non-volatile data storage unit. Additionally, a real time display unit may be provided for displaying, in real time, a correlated signal output by the mixer.

The system of the present invention may also include a panic button. A panic button marker signal is input to the mixer when the panic button is actuated, and the panic button marker signal is temporally correlated and mixed by the mixer with the video and audio feed and the signals based on brain waves.

The sensors of the present invention may include a cup structure; an electrode disposed in the cup structure; and a conductive gel injection port for injecting a conductive gel into the cup structure to make electrical contact between the electrode and a portion of a scalp of a patient whose brain waves are to be monitored.

The headgear of the present invention may have a fastener such covering its interior. Sensors and pads may be located and secured as needed to the fastener in the headgear. Each sensor may be associated with an inflatable pad that inflates to hold the sensor comfortably and securely between the headgear and the patient's scalp.

The present invention also encompasses a method for monitoring brain waves by: disposing a plurality of sensors around a scalp of a patient whose brain waves are to be monitored; generating signals based on the patient's brain waves with the sensors; transmitting the signals to a processor over a wireless link; and receiving and processing the transmitted signals with the processor.

The present method may include disposing the plurality of sensors in a skull cap worn by the patient, the skull cap having a polydirectional antenna for establishing the wireless link. The method may also include multiplexing the signals prior to transmission with a multiplexer disposed on the skull cap, and encoding the signals prior to transmission with an encoder disposed on the skull cap. For different patients, the method may include adjusting the size of the skull cap. Additionally, the method may involve testing the operation of the skull cap through a test port.

The present method may further include generating a video and audio feed of the patient with a video camera. Given such a feed, the method may include receiving the transmitted signals with a plurality of receivers; processing the video and audio feed with a processing circuit; mixing the signals and the feed with a mixer; and temporally correlating the signals and the feed with a synchronizing circuit which controls the mixer. The method may further include controlling the operation of the video camera with a control signal from the processing circuit.

After mixing, the method may include storing a correlated signal output by the mixer in a non-volatile data storage unit, and compressing the correlated signal prior to storage in the non-volatile data storage unit. After storage, the method may include editing, annotating or analyzing the correlated signal stored in the non-volatile data storage unit with a computer.

The method of the present invention may also include displaying, in real time, a correlated signal output by the mixer, the correlated signal comprising the audio and video feed and the signals based on brain waves.

The present method may also include inputting a panic button marker signal to the mixer when a panic button is actuated; and temporally correlating and mixing the panic button marker signal with the audio and video feed and the signals based on brain waves.

The method of the present invention may include injecting a conductive gel into a cup structure of each of the sensors to make electrical contact between an electrode disposed in the cup structure and a portion of the scalp of the patient.

Finally, the method of the present invention may include attaching sensors and pads to the interior of the headgear in appropriate locations and inflating pads, each of which is associated with a sensor, to secure the sensor between the headgear and the patient's scalp.

BRIEF DESCRIPTION OF THE DRAWINGS

The accompanying drawings illustrate the present invention and are a part of the specification. Together with the following description, the drawings demonstrate and explain the principles of the present invention. In the drawings.

DETAILED DESCRIPTION OF THE PREFERRED EMBODIMENT

Figure 1:
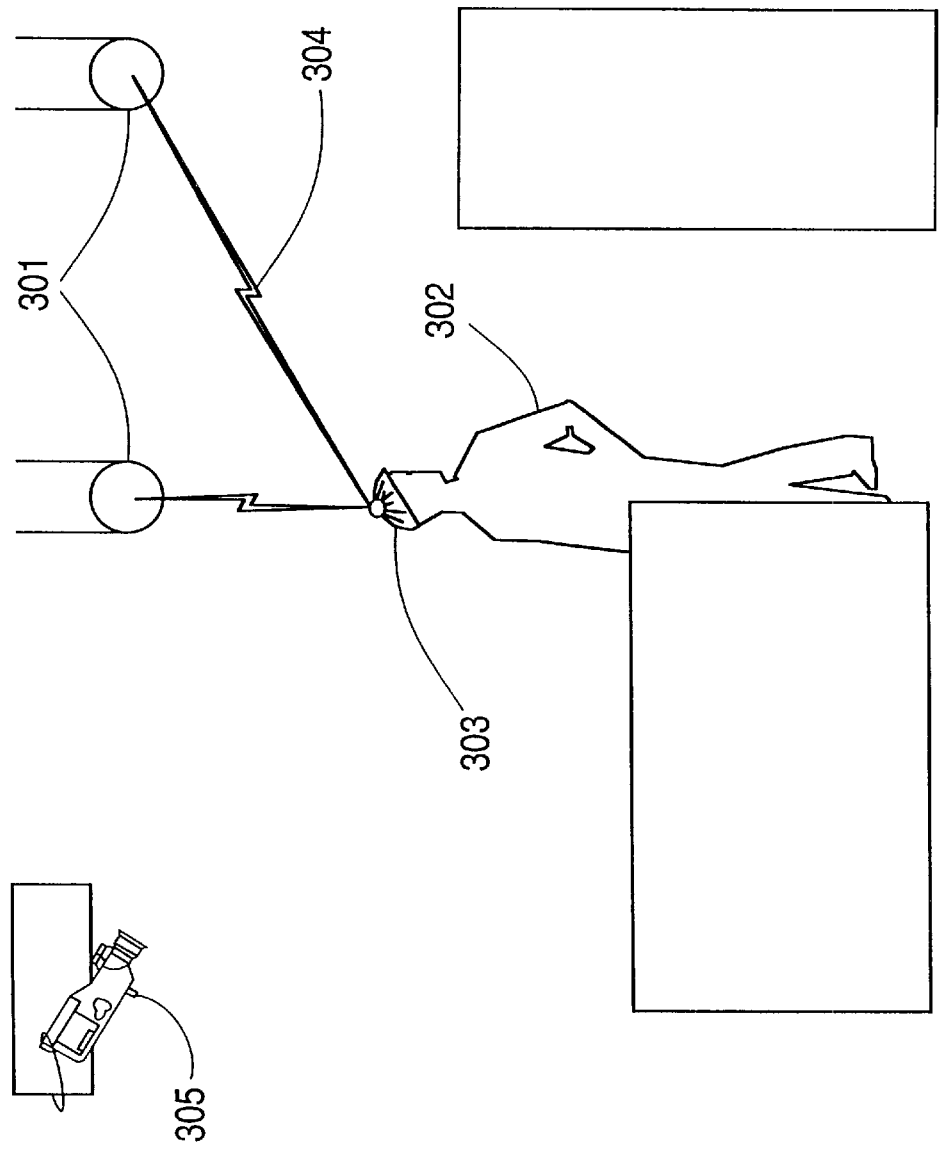
FIG. 1 illustrates the system of the present invention.

Using the drawings, the preferred embodiment of the present invention will now be explained. As shown in FIG. 1, the present invention provides a method and system of wirelessly monitoring the brain wave activity of a patient 302. The patient 302 is fitted with a piece of headgear. The headgear may be, for example, a skull cap 303, as pictured in FIG. 1. The headgear may also be a helmet which will be described in detail below. The skull cap 303 maintains contact between a plurality of sensors and the patient's scalp.

The patient's brain wave activity is detected by these sensors and transmitted over a wireless link 304 from the skull cap 303 to one of several receivers 301 disposed around the room in which the patient 302 is being monitored. The transmission 304 may be, for example, an infrared light signal, a radio frequency signal, or any other type of transmission that will not interfere with other electronic equipment in the hospital or clinic where the patient 302 is being monitored.

The method and system of the present invention may also include a video camera 305 which makes a video and audio recording of the patient 302 while the patient 302 is being monitored. In this way, the diagnosing physician can correlate abnormal or distressed behavior in the patient 302, as recorded by the video camera 305, with abnormal brain wave activity, as detected by the sensors of the skull cap 303.

As an advantage, the system of the present invention allows the patient 302 to move freely about the room while his or her brain wave activity is monitored. The patient need not be restrained by being wired to an immobile EEG machine and, therefore, may be much more comfortable during a prolonged monitoring session.

Additionally, the components of the present invention may be made portable so that they can be transported, for example, to the patient's home. In this way, the patient can be monitored at home in familiar surroundings and less stressful circumstances.

A detailed explanation of the skull cap 303 of the present invention will now be provided. The skull cap 303 can be made adjustable with regard to size by constructing it from an elastic material such as Spandex®, and by providing, for example, a series of straps around the cap that can be taken in or loosened as needed. In this way, the skull cap can be used with a variety of patients of different ages and sizes. The wide range of possible strap combinations or other means of making the skull cap 303 adjustable in size are considered readily apparent and within the ambit of one skilled in the art, and will not be explained further herein.

Figure 2:
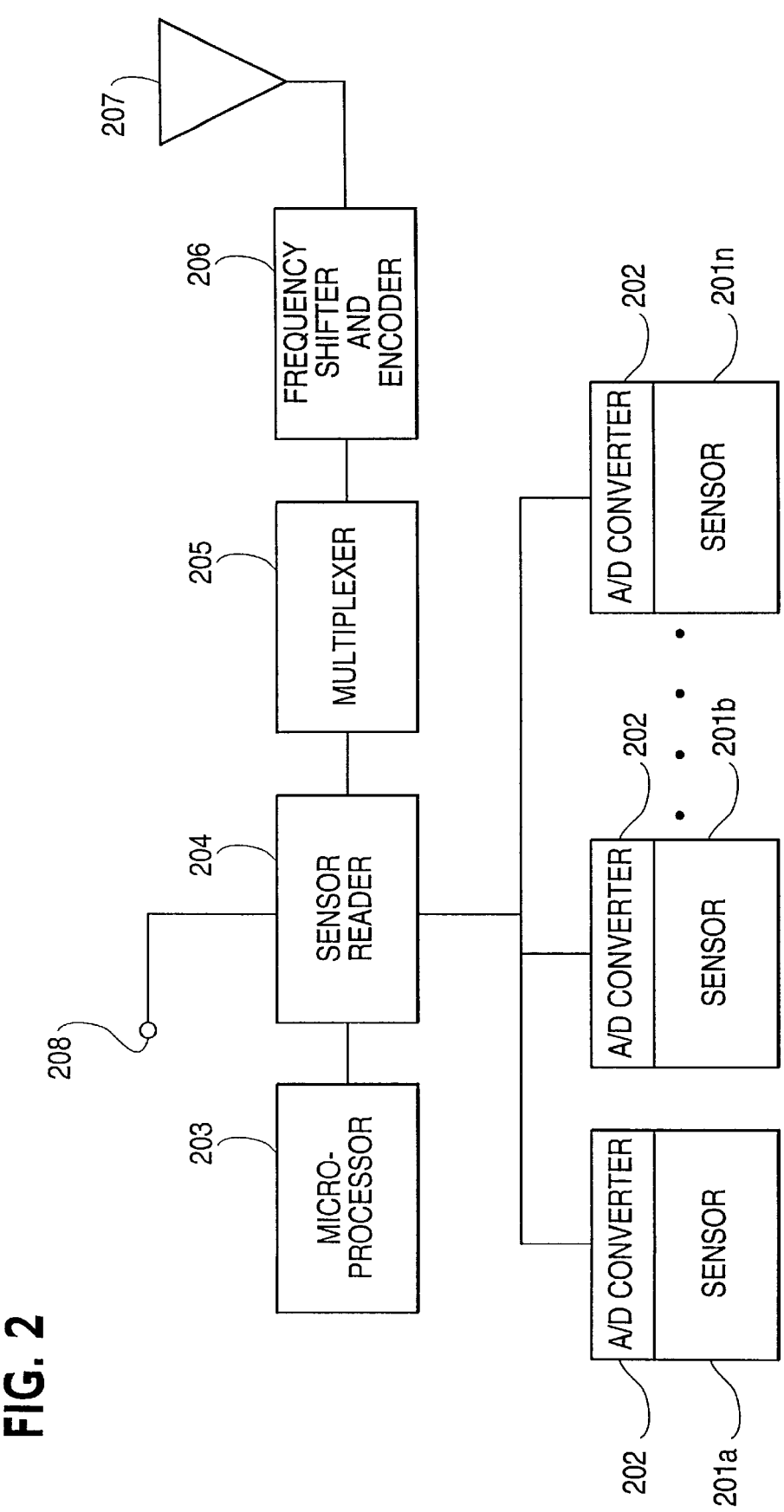
FIG. 2 is a block diagram of the circuitry in a skull cap of the present invention.

FIG. 2 is a block diagram of the circuitry of the skull cap 303. As described above, a plurality of sensors 201a to 201n are provided in the cap so as to make contact with the scalp of the patient when the cap 303 is worn. During fitting of the cap and initialization of the system each electrode is provided with an identify code indicating its position and hence correlating with a brain region of interest. Alternatively, each sensor may have a preset identify code to speed up fitting. A present identify code will not be overwritten unless a different arrangement of sensors is desired.

Each sensor is preferably provided with an A/D convertor 202 for converting the analog brain wave signal detected in the patient by the sensor 201 into a digital signal which is then processed by the system. The sensors 201 and A/D convertors 202 are wired to a sensor reader circuit 204 which is controlled by a microprocessor 203.

The signals indicative of brain wave activity obtained from the various sensors 201 are multiplexed with multiplexer 205. The data may then by frequency shifted and encoded by a circuit 206. As an alternative, the frequency shifting and encoding may be performed before the signals are multiplexed. Finally, the encoded, multiplexed data is transmitted by a polydirectional antenna 207. The polydirectional antenna 207 may be, for example, a radio frequency antenna or an infrared light source, depending on the type of electromagnetic waves chosen to establish the wireless link 304.

A test and initializing port 208 is preferably provided by which test data is input to the sensor reader 204 and identification codes may be assigned to each sensor under control of microprocessor 203. In this way, a test can be performed to ensure that the circuitry of the skull cap is functioning properly.

Figure 3:
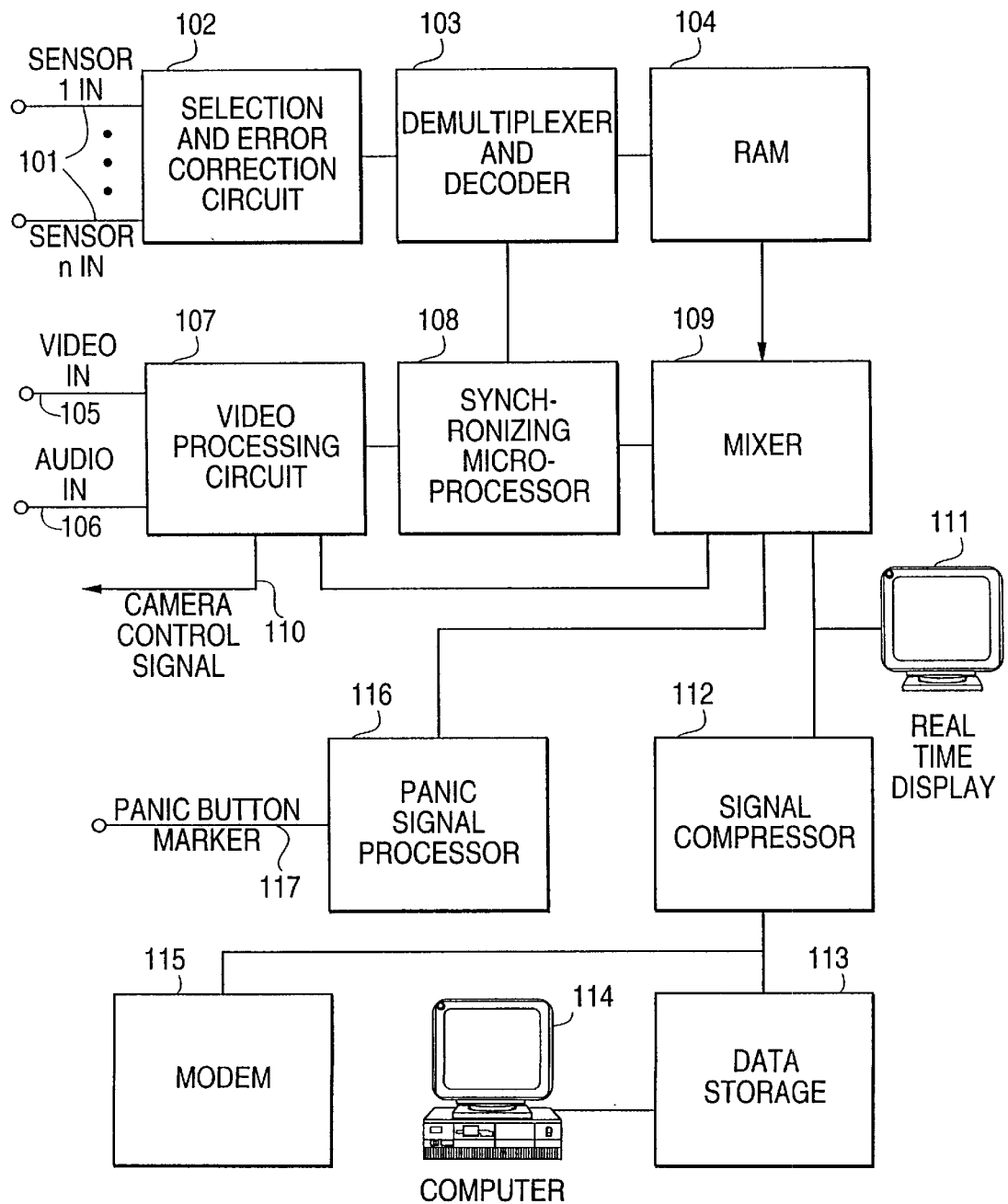
FIG. 3 is a block diagram of the supporting system of the present invention.

FIG. 3 illustrates the system which supports the skull cap of the present invention. After the multiplexed data is transmitted by the polydirectional antenna 207, it is received by the receivers 301 shown in FIG. 1. The signals 101 received by these receivers 301 are feed to a selection and error correction circuit 102. The circuit 102 selects the receiver 301 which is receiving the best or strongest signal from the skull cap. This will typically be the receiver 301 which is physically closest to the current location of the skull cap 303 and patient 302. The circuit 102 will then use the output of that receiver 301 and perform any error correction processing necessary to improve the signal.

After selection and error correction, the signal is demultiplexed and decoded by a demultiplexing and decoding circuit 103. The demultiplexed and decoded signal is then stored in RAM 104 or an equivalent memory storage unit. For rewritable storage of large amounts of data, magneto-optical disks may be preferable.

The video feed 105 and audio feed 106 from the video camera 305 (shown in FIG. 1) are received by a video processing circuit 107. The video processing circuit may also generate a camera control signal 110 which is returned to the camera. The camera control signal 110 may adjust the operation of the camera, e.g., angle, zoom, focus, etc. to better record the activity of the patient 302.

The video and audio feeds and the recorded brain wave activity stored in the RAM 104 are input to a mixer 109. A synchronizing microprocessor 108 monitors the demultiplexer/decoder 103 and the video processing circuit 107 and controls the mixer 109 so that the audio/video feed and the brain wave signals are temporally correlated by the mixer.

The system may also include a panic button which the patient or an attendant can press in the event of patient distress. This allows the association of the relevant period of brain wave activity of the patient with an emotional or physical episode experienced by the patient. When the panic button is pressed, a panic button marker signal 117 is sent to a panic signal processor 116. The panic signal processor 116 feeds the indication of a panic signal to the mixer 109 so that a "panic marker" can be mixed with the brain wave signals and audio/video feed.

The combined data is output by the mixer 109 to a real time display 111 which provides a display of the combined and correlated brain wave signals, audio/video feed, and panic marker signal to the diagnosing physician/technician in real time. The output of the mixer 109 is also provided to a signal compressor 112 which compresses the data for storage. For example, the video data may be compressed using the internationally recognized MPEG method developed by the Moving Pictures Expert Group of the International Standards Organization.

After compression, the correlated data is stored in a non-volatile data storage unit 113. The data in storage unit 113 is then accessible by computer 114 and may be transmitted via modem 115 over a standard telephone line and a Public Switched Telephone Network (PSTN), or other public or dedicated network, to a consulting physician, central archive, etc.

The computer 114 may be provided with software for editing and annotating the patient's brain wave record. Such software may also preferably include automatic wave form recognition functions which will analyze the record against a database of irregularities of known causes and flag sections of the record for special attention by the physician. Preferably, such functions will operate at greater than real time speeds without using expensive physician time.

The computer 114 may also be provided with software with which a wave form analysis of the patients's brain wave record may be performed by the physician. Desirable functions include searching the entire record for a match (or fuzzy logic similarity) for a particular episode, and allowing nonlinear viewing/selection of multiple episodes. Such software and the knowledge needed to create it from the variety of possible approaches are considered within the ambit of one skilled in the art and are, therefore, not described further herein.

Figure 4:
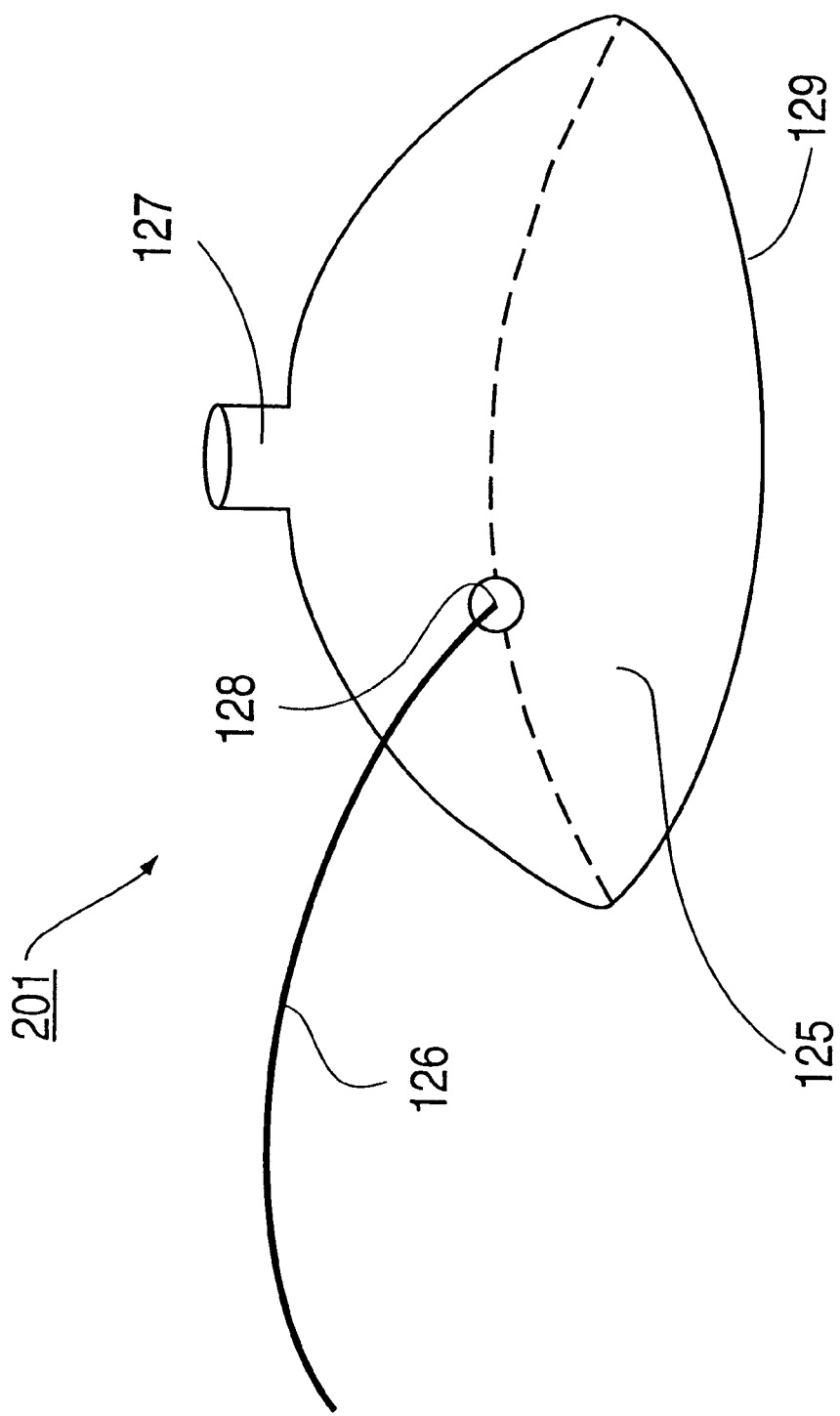
FIG. 4 illustrates an individual sensor from the skull cap of the present invention.

FIG. 4 illustrates an exemplary sensor, a plurality of which are provided in the skull cap 303 of the present invention. Positions of the elements of the sensor, its shape, size, etc., are exemplary only and capable of modification by those skilled in the art. For example, hexagonal sensors with the electrode 128 and wire 126 entering through an injection port 127 are also acceptable.

The sensor 201 preferably comprises a cup structure 125 in which an electrode 128 is provided. A wire 126 connects the electrode 128 to the circuitry of the skull cap as illustrated in FIG. 2. The placement of the A/D convertor 202 may be at the site of the electrode 128 or elsewhere along the connection wire 126.

The cup structure 125 of the sensor 201 further comprises an injection port 127. When the skull cap 303 is sized and placed on the head of the patient 302, the rim 129 of the cup 125 is held in contact with the scalp of the patient 302. A conductive gel is then injected in the injection port 127 until the cup 125 is filled. Standard medically approved gels are acceptable, with lower viscosity gels being preferable for longer testing.

When injected, the conductive gel creates an electrical connection between the electrode 128 and the scalp of the patient 302. In this way, the brain wave activity of the patient 302 can be detected and monitored through the electrode 128. Using the test port 208 and standard tests h/w and s/w, the functioning of each electrode may be confirmed including its positioning, immobility in relation to the patient's brain, and the connection formed by the gel and cup structure.

Figure 5:
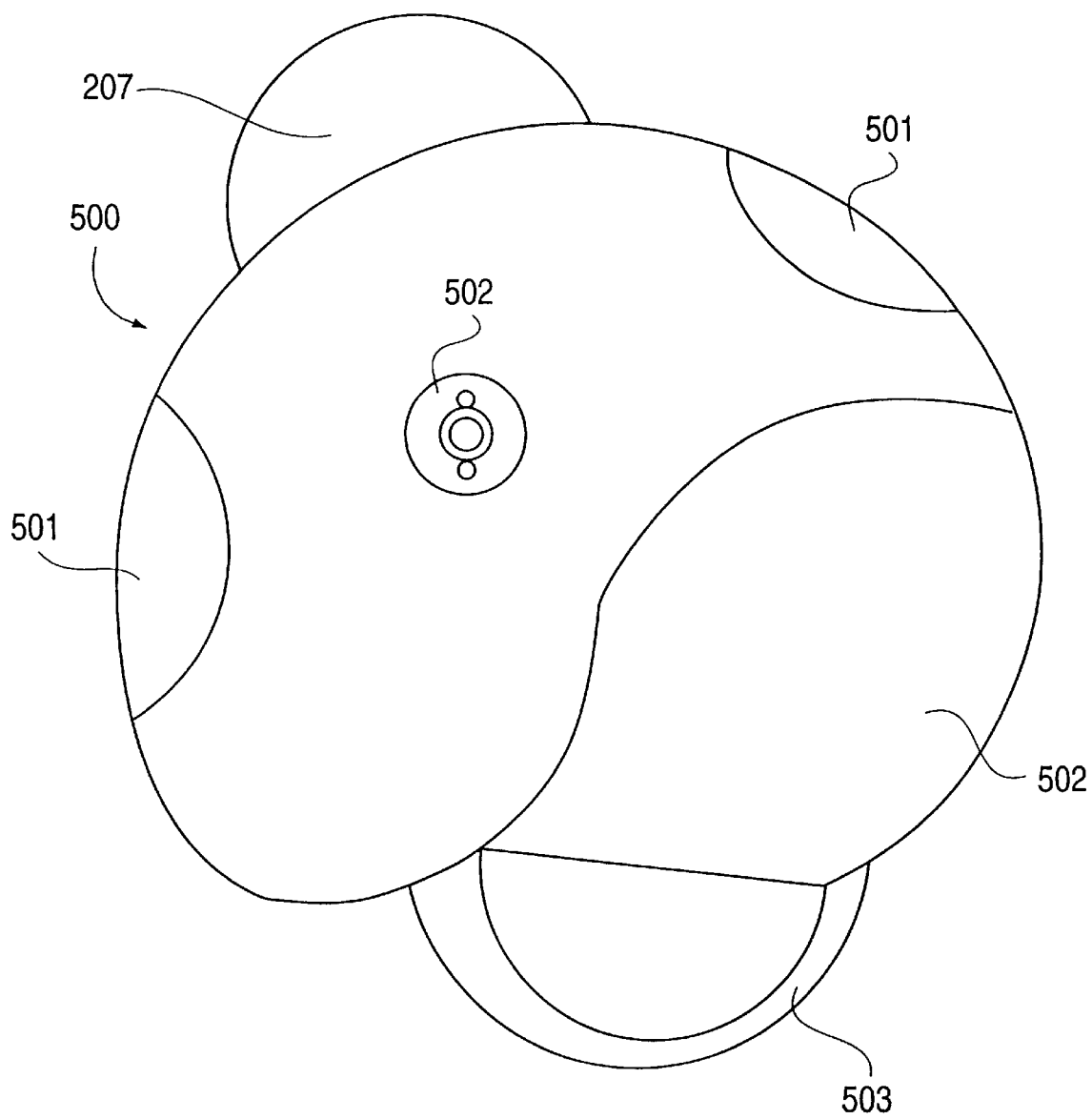
FIG. 5 illustrates a helmet according to the present invention.
Figure 6:
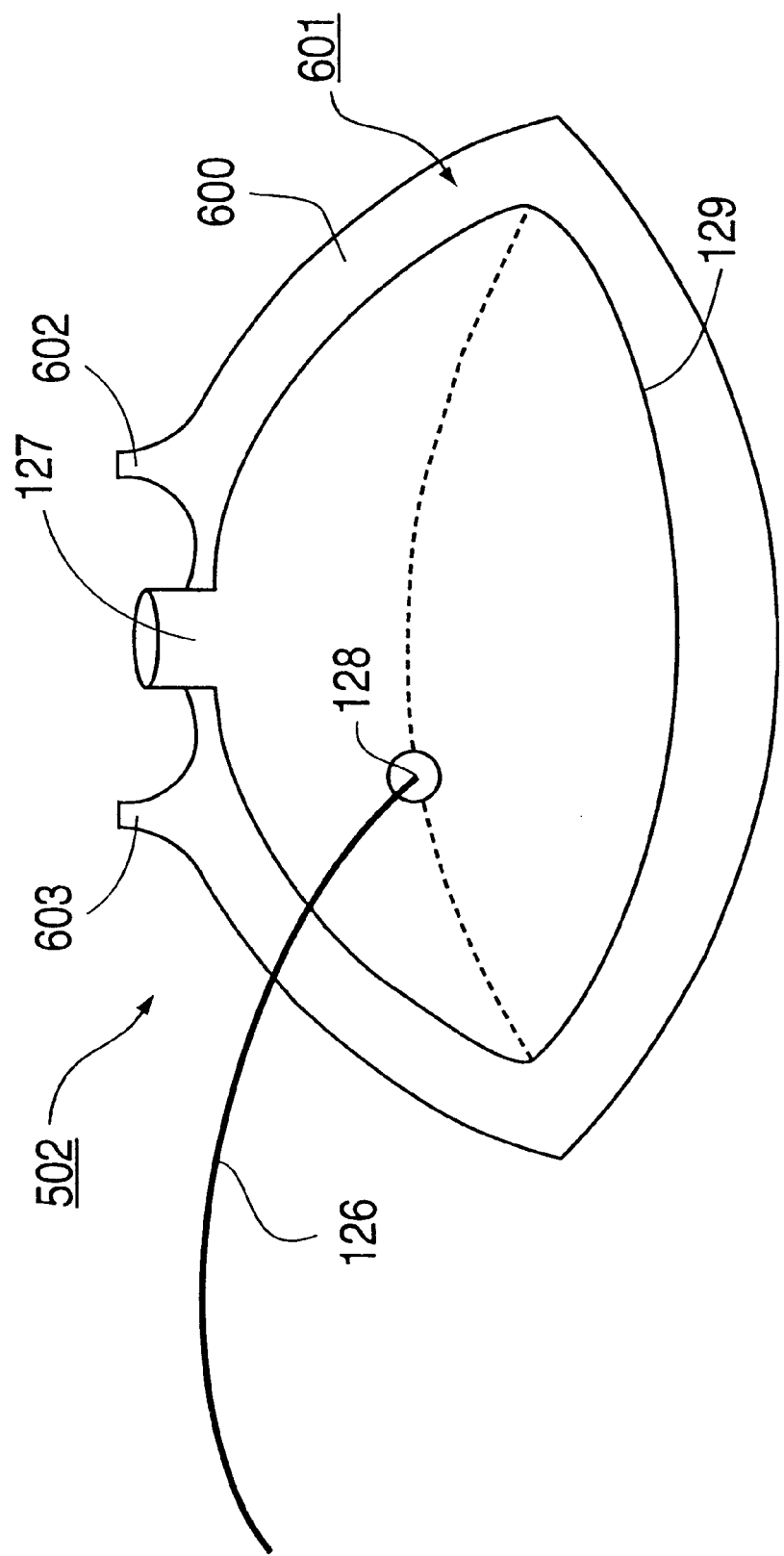
FIG. 6 illustrates a padded sensor according to the present invention for use with the helmet illustrated in FIG. 5.

FIGS. 5 and 6 illustrate an additional embodiment of the present invention which is similar to the embodiment described above with the exception that the headgear used is a helmet 500 rather than a skull cap.

As shown in FIG. 5, the helmet has a hard outer shell, somewhat like a football or bicycle helmet. The polydirectional antenna 207 and the other circuitry described above are also mounted on the helmet 500. Additionally, the interior of the helmet 504 is covered with fasteners, e.g., velcro™, snaps, grooves etc. with which pads 501 and sensors 502 can be attached at various points as needed to the interior of the helmet.

The pads 501 are of a fixed size and may be permanently secured inside the helmet or may be detachable so that differently sized pads can be secured in the helmet using the above-mentioned fasteners to make it more comfortable for differently sized patients. A securing mechanism, for example, an adjustable chin strap 503, is also provided to comfortably secure the helmet 500 to a patient's head.

The sensors 502 for use with the helmet 500 are illustrated in detail in FIG. 6. The sensors 502 are similar to the sensors 201 described previously with the principal exception of being associated with an adjustable sensor locating pad 600 (ASLP) which is provided to position and hold the sensor 502.

The pad 600 surrounding the sensor cup 129 is inflatable. Inflating the pad 600 allows it to comfortably hold the sensor 502 between the helmet and the patient's scalp, while maintaining the essential contact between sensor and scalp. Preferably, the pad 600 has an air inlet port 603 and a bleed port 602, in addition to a gel injection port 127. The inlet port and bleed port may be combined into a single port, however, doing so will increase the time required to properly inflate the pad 600.

The exterior of the pad 600 is also provided with a fastening means 601, such as velcro, snaps or grooves, to mate to the fasteners in the interior of the helmet 504. Accordingly, sensors 502 and associated pads 600 can be secured inside the helmet at those positions necessary to monitor the patient's brain activity.

After positioning and securing the pads 600 and sensors 502 inside the helmet 500, the pad 600 is inflated for a tight fit using the inlet port. Next, the conductive gel is injected, and the sensor is tested. Alternating use of the air inlet port 603 and bleed port 602 provide the desired fit.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A system for monitoring brain waves comprising:
   a plurality of sensors for generating signals based on brain waves;
   a wireless infrared link for transmitting said signals to a processor; and
   a processor for receiving said transmitted signals and for processing said signals so as to analyze said brain waves and generate a record of said brain waves;
   wherein said sensors and said wireless infrared link are interconnected and mounted as a self-contained unit which is wearable by a patient whose brain waves are being monitored so as to allow said patient unrestricted movement within a range of said wireless link without a physical connection to any additional monitoring equipment; and
   wherein said plurality of sensors are disposed in a piece of headgear, said headgear comprising a polydirectional infrared transmitter for establishing said wireless link.

2. A system as claimed in claim 1, wherein said headgear further comprises a multiplexer for multiplexing said signals prior to transmission.

3. A system as claimed in claim 1, wherein said headgear further comprises an encoder for encoding said signals prior to transmission.

4. A system as claimed in claim 1, said headgear further comprising a test port through which test signals may be input to test the operation of said sensors.

5. A system as claimed in claim 1, further comprising a video camera for providing video and audio feed of a patient whose brain waves are being monitored.

6. A system as claimed in claim 5, wherein said processor further comprises:
   a plurality of receivers for receiving said transmitted signals;
   a processing circuit for receiving said video and audio feed;
   a mixer for mixing said signals and said feed; and
   a synchronizing circuit which controls said mixer, causing said mixer to temporally correlate said signals and said feed.

7. A system as claimed in claim 6, wherein said processor further comprises a non-volatile data storage unit for storing a correlated signal output by said mixer.

8. A system as claimed in claim 7, wherein said processor further comprises a signal compressor for compressing said correlated signal prior to storage in said non-volatile data storage unit.

9. A system as claimed in claim 7, further comprising a computer for editing, annotating or analyzing said correlated signal stored in said non-volatile data storage unit.

10. A system as claimed in claim 6, further comprising a real time display unit for displaying in real time a correlated signal output by said mixer, said correlated signal.

11. A system as claimed in claim 6, further comprising a panic button, wherein a panic button marker signal is input to said mixer when said panic button is actuated, said panic button marker signal being temporally correlated and mixed by said mixer with said video and audio feed and said signals based on brain waves.

12. A system as claimed in claim 1, wherein said headgear is a skull cap which is adjustable to a range of sizes.

13. A system as claimed in claim 2, wherein said headgear is a helmet.

14. A system as claimed in claim 13, wherein each of said sensors is associated with an inflatable pad which can be secured at a variety of locations on an interior of said helmet.

15. A system as claimed in claim 6, wherein said processing circuit generates a camera control signal to control the operation of said video camera.

16. A system as claimed in claim 1, wherein said sensors comprise:
   a cup structure;
   an electrode disposed in said cup structure; and
   a conductive gel injection port for injecting a conductive gel into said cup structure to make electrical contact between said electrode and a portion of a scalp of a patient whose brain waves are to be monitored.

17. A method for monitoring brain waves comprising:
   disposing a plurality of sensors around a scalp of a patient whose brain waves are to be monitored, wherein said disposing further comprises disposing said plurality of sensors in a piece of headgear worn by said patient, said headgear comprising a polydirectional infrared transmitter for establishing a wireless link;
   generating signals based on said patient's brain waves with said sensors;
   transmitting said signals to a processor over said infrared wireless link;

receiving and processing said transmitted signals with said processor to analyze and generate a record of said brain waves; and allowing said patient whose brain waves are being monitored unrestricted movement within a range of said wireless link without a physical connection to any additional monitoring equipment by interconnecting and mounting said sensors and said wireless infrared link as a self-contained unit which is wearable by said patient.

18. A method as claimed in claim 17, further comprising multiplexing said signals prior to transmission with a multiplexer disposed on said headgear.

19. A method as claimed in claim 17, further comprising encoding said signals prior to transmission with an encoder disposed on said headgear.

20. A method as claimed in claim 17, further comprising testing the operation of said sensors through a test port.

21. A method as claimed in claim 17, further comprising generating a video and audio feed of said patient with a video camera.

22. A method as claimed in claim 21, wherein said receiving and processing further comprises:

receiving said transmitted signals with a plurality of receivers;

processing said video and audio feed with a processing circuit;

mixing said signals and said feed with a mixer; and temporally correlating said signals and said feed with a synchronizing circuit which controls said mixer.

23. A method as claimed in claim 22, further comprising storing a correlated signal output by said mixer in a non-volatile data storage unit.

24. A method as claimed in claim 23, further comprising compressing said correlated signal prior to storage in said non-volatile data storage unit.

25. A method as claimed in claim 23, further comprising editing, annotating or analyzing said correlated signal stored in said non-volatile data storage unit with a computer.

26. A method as claimed in claim 22, further comprising displaying in real time a correlated signal output by said mixer, said correlated signal comprising said audio and video feed and said signals based on brain waves.

27. A method as claimed in claim 22, further comprising:

inputting a panic button marker signal to said mixer when a panic button is actuated; and temporally correlating and mixing said panic button marker signal with said audio and video feed and said signals based on brain waves.

28. A method as claimed in claim 18, further comprising adjusting a size of said headgear.

29. A method as claimed in claim 18, further comprising securing said plurality of sensors around an interior of said headgear as needed to monitor brainwave activity.

30. A method as claimed in claim 29, further comprising inflating a pad associated with each sensor.

31. A method as claimed in claim 22, further comprising controlling the operation of said video camera with a control signal from said processing circuit.

32. A method as claimed in claim 17, further comprising injecting a conductive gel into a cup structure of each of said sensors to make electrical contact between an electrode disposed in said cup structure and a portion of said scalp of said patient.

* * * * *